United States Patent [19]

Howe et al.

[11] Patent Number: 5,164,675
[45] Date of Patent: Nov. 17, 1992

[54] FLUID PRESENCE DETECTOR FOR GAS PIPE USING AN EXCITED WIRE MESH

[75] Inventors: Bradford H. Howe, Vergennes; William E. Dunn, Monkton, both of Vt.

[73] Assignee: Simmonds Precision Products, Inc., Akron, Ohio

[21] Appl. No.: 869,855

[22] Filed: Apr. 16, 1992

Related U.S. Application Data

[63] Continuation of Ser. No. 743,829, Aug. 12, 1991, abandoned.

[51] Int. Cl.$^5$ .............................................. G01R 27/26
[52] U.S. Cl. ..................................... 324/690; 324/663; 324/664; 324/686; 324/689; 73/29.01
[58] Field of Search .............. 324/663, 664, 686, 688, 324/689, 690; 73/29.01, 29.02, 29.05

[56] References Cited

U.S. PATENT DOCUMENTS

| | | | |
|---|---|---|---|
| 2,911,576 | 11/1959 | De Giers | 324/690 X |
| 3,046,537 | 7/1962 | Dow | 340/234 |
| 3,238,452 | 3/1966 | Schmitt et al. | 324/686 X |
| 3,424,977 | 1/1969 | Krobath | 324/689 |
| 4,168,465 | 9/1979 | Prince | 324/690 X |
| 4,520,667 | 6/1985 | Nelson | 73/171 |
| 4,644,263 | 2/1987 | Johnson | 324/446 |
| 4,658,208 | 4/1987 | Lee et al. | 324/717 |
| 4,882,648 | 11/1989 | Verrando, III | 324/690 X |

Primary Examiner—Jack B. Harvey
Assistant Examiner—Glenn W. Brown
Attorney, Agent, or Firm—Leonard L. Lewis; David M. Ronyak

[57] ABSTRACT

A liquid presence detector and method of using the same for a gas fluid conduit is provided by a capacitor that is placed inside the conduit and that is formed of two interwoven wire grids with one of the grids being insulated and the other grid being uninsulated. In one embodiment, the capacitor is generally planar and is oriented generally transverse a longitudinal axis of the conduit with a peripheral portion lying in a generally axial orientation along an inner surface of the conduit. A circuit is provided that measures capacitance between the two wire grids. The conduit is electrically grounded. Liquid particles entrained in the gas fluid or traveling along the conduit wall contact the capacitor and changes the capacitance thereof. In another embodiment, the capacitor is formed as a generally open cylinder positioned coaxially within the conduit. A flow distributor is positioned within a portion of the cylinder and directs gas flow and liquid particle movement in a non-axial direction for contact with the capacitor.

20 Claims, 2 Drawing Sheets

FLUID PRESENCE DETECTOR FOR GAS PIPE USING AN EXCITED WIRE MESH

This is a continuation of copending application Ser. No. 07/743,829 filed on Aug. 12, 1991, now abandoned.

BACKGROUND OF THE INVENTION

The present invention relates generally to fluid conduits used to conduct or transport substances in gaseous form from one location to another. More specifically, the invention relates to providing a liquid presence detector for gaseous fluid conduits, which conduits are intended to function without the presence of liquid therein.

Many types of apparatus require the use of gas-filled fluid conduits that are not intended to have any liquid or condensate in the gas fluid. A typical example is a "gas only" output line for a water reclamation system. The presence of liquid in the gas provides an indication that there is a leak or other failure in the separator apparatus. Liquids such as water can also be undesirable in gas feed lines. Water may occur due to direct leaks into the gas line, or from condensation of water vapor that is either present in the gas or that enters the conduit through some other means. A liquid recovery system or a liquid separator is typically included with such a gas line to extract the unwanted liquid. These liquid extraction systems may require an actuation signal that indicates to the apparatus that liquid is present in the conduit or entrained in the gas. In highly controlled and sophisticated systems such as those used in connection with the space program, even small droplets or particles of liquids such as water can damage equipment. Furthermore, systems that are intended for use in space require a liquid detector that can function accurately and reliably in a substantially weightless environment.

A common problem with sensors and detectors that use electrical signals or properties such as resistance, capacitance and inductance is the presence of electromagnetic interference and general background electrical noise that cause false or erroneous readings. Such radiated noise can be coupled into a circuit and appear as false or spurious voltage and current spikes. This is especially true in space applications where exposure to high radiation levels is more common.

Another important feature of a liquid detection device is that it should be able to detect accurately liquid that is traveling along the inner conduit surface or wall. Particularly in a weightless environment, the liquid particles tend to be pushed away from the primary gas towards the conduit wall, and then travel along the conduit wall under motive force from the gas moving through the conduit. In larger pipes and conduits, however, some liquid particles may stay entrained in the gas fluid and a liquid presence detector should be able to detect such entrained particles as well.

SUMMARY OF THE INVENTION

The present invention contemplates a liquid detector for fluid conduits that detects liquid particles that travel along the wall or inner surface of the conduit, as well as liquid particles that are entrained in a gas fluid. The invention is particularly suited for use in conduits that carry gaseous fluids and are intended to be liquid free. The present invention also contemplates a liquid detector that can be used in substantially weightless environments such as a space station, yet is relatively immune from the effects of electromagnetic interference and reduces the risk of electric shock.

The invention contemplates a liquid detector for a gaseous fluid conduit that utilizes the dielectric effect of liquids such as water to affect the capacitance of a capacitive element in the detector. According to this aspect of the invention, the detector is placed in the conduit in such a manner that liquid particles entrained in the gas fluid will contact a portion of the detector. The detector is also positioned within the conduit so as to contact fluid particles that travel along the inner surface of the conduit. When one or more liquid particles contact the detector, the capacitance of the detector is changed and can be measured by a capacitance circuit connected to the detector through an opening in the conduit.

A liquid detector according to the present invention includes a capacitor sensor that is conveniently positioned within a section of the conduit being monitored. The capacitor sensor preferably is in the form of a wire mesh or screen that may be appropriately sized and shaped for the particular conduit with which it will be used. In one embodiment, the capacitor sensor is a generally planar element realized by a pair of interwoven wire grids. Each wire grid serves as one plate of the capacitor sensor with one of the grids being composed of uninsulated wire, and the other grid being composed of insulated wire. The grids are interwoven with the insulated wire preferably being disposed transverse the uninsulated wire in a criss-crossing type pattern. The wire mesh design is configured with a predetermined mesh size so that liquid particles that contact the grids will bridge at least one insulated and uninsulated pair of wires thereby changing the capacitance of the overall sensor. Each wire grid can be formed from a single wire that is looped back and forth when interwoven with the other grid, or each grid can be formed from a plurality of wires that lie generally parallel to each other. The planar sensor is preferably positioned within the conduit transverse the conduit's longitudinal axis so as to capture liquid particles entrained in the gas fluid. The wire mesh also includes a peripheral flange portion that is bent over to lie generally flush against the inner surface of the conduit. The peripheral flange lies against the conduit inner surface and contacts liquid particles that travel along the inner surface.

In another embodiment, the capacitor sensor is again realized in the form of a wire mesh or screen, however, the wire mesh is generally cylindrical in shape and is inserted coaxially in the conduit. The wire mesh has two interwoven wire grids with one grid being insulated wire and the other grid being uninsulated wire. The cylindrical sensor is positioned within the conduit in such a manner that liquid particles entrained in the gas fluid are forced into contact with the wire mesh, and liquid particles traveling along the conduit inner surface also contact the wire mesh. The liquid particles bridge at least one pair of insulated and uninsulated wires so as to change the capacitance of the overall capacitor sensor. A flow distributor can be provided to improve the directional flow of the entrained liquid particles towards the wire mesh.

The present invention also contemplates a liquid presence detector that is shielded from the effects of electromagnetic interference and reduces the risk of electrical shock from contact with the conduit. According to this aspect of the invention, the conduit is electrically grounded and shields the liquid detector that is positioned inside the conduit from electromagnetic interference. The grounded conduit also reduces the risk of electrical shock to nearby personnel since the liquid detector can be operated with a circuit that applies voltage to the capacitor grid while the conduit remains at ground potential. Because the grid includes uninsulated wires in contact with the conduit insulated surface, one plate of the capacitor sensor is always at ground potential.

The present invention also contemplates a new method for detecting liquid particles in a gas fluid conduit. This method includes the steps of forming a capacitor sensor from a pair of interwoven wire grids with one grid being insulated wire and the other grid being uninsulated wire; placing the capacitor sensor in the conduit and using the wire grid to detect liquid particles that travel along the inner surface of the conduit as well as liquid particles that are entrained in the gas fluid; connecting the conduit to electrical ground and placing the wire grid sensor in the conduit in such a manner that uninsulated wires of the grid contact the conduit; and measuring changes in the capacitance of the wire grid due to contact of liquid particles with the grid.

These and other aspects and advantages of the present invention will be apparent to those skilled in the art from the following detailed description of the invention in view of the accompanying drawings.

DESCRIPTION OF THE PREFERRED EMBODIMENTS

Figure 1:
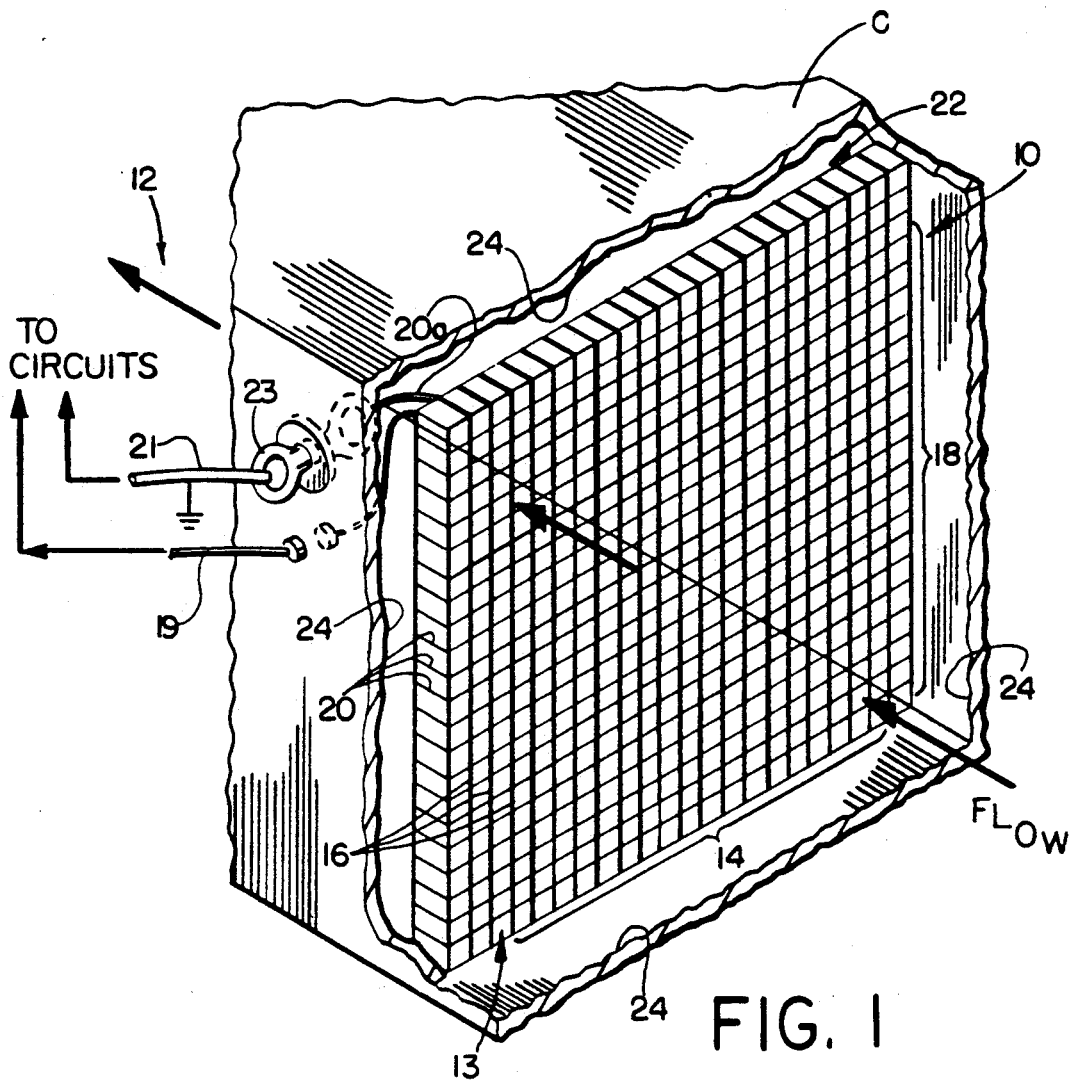
FIG. 1 is a perspective schematic of a liquid presence detector according to the present invention positioned in a gas fluid conduit shown in partial section.

With reference to FIG. 1, a liquid presence detector 10 according to the present invention is illustrated positioned in a gaseous fluid conduit "C" with only a portion of the overall conduit being shown in FIG. 1. The conduit may be made of any size and material suitable for transporting gaseous fluid from one location to another. For example, the conduit may be a "gas only" output pipe from a water reclamation system. While the present invention is described herein with reference to detecting water particles or drops in an air conduit, those skilled in the art will readily appreciate that the present invention is not limited to only the exemplary application so described. The present invention can be applied to other systems in which it is desired to detect the presence of a liquid, be it water or other liquid, entrained in a gas or adhering to a gas conduit wall.

In the embodiment illustrated in FIG. 1, the detector 10 is positioned in the conduit transverse a central longitudinal axis 12 of the conduit. Thus, the detector 10 lies transverse the flow line of gas traveling through the conduit. Fluid particles entrained in the gas can contact the detector 10 without an appreciable drop in gas pressure or velocity as the gas passes through the detector 10. The mesh is preferably formed to the shape of the conduit. In the example of FIG. 1, the air duct is generally rectangular so the mesh is formed with a rectangular shape. With a round duct or pipe the mesh could be made circular.

The liquid presence detector 10 is generally a planar element having two wire grids interwoven into a mesh or screen 13 configuration. A first wire grid 14 is formed by a series of parallel insulated wires 16, which are oriented in the vertical direction in FIG. 1. A second wire grid 18 is formed by a series of parallel uninsulated wires 20, which are oriented in a horizontal direction in FIG. 1. The insulated wires 16 are drawn somewhat thicker in FIG. 1 as compared to the uninsulated wires 20. Thus, the two wire grids 14,18 lie transverse each other and are interwoven such that the detector 10 is a capacitor sensor that is an alternating planar pattern of insulated and uninsulated wires. Each grid 14,18 forms one plate of a two plate capacitor.

Those skilled in the art will readily appreciate that the wire grids 14,18 need not be oriented transverse each other to form a capacitor, however, the transverse orientation simplifies manufacture of the interwoven mesh. The mesh size, i.e. the spacing between adjacent wires, can be chosen in relation to the size of liquid particles to be detected and the degree to which gas flow restriction can be tolerated. For example, the invention has been successfully realized with a mesh size of 10 wires per inch (10 mesh) to detect liquid particles on the order of 0.05 cc in a 1.5 inch gas pipe at a gas flow rate of 20 feet per second. Reducing the mesh size will increase the sensitivity of the detector 10 to smaller particles, though at some point the smaller mesh may result in a restricted gas flow. The tradeoffs will be determined as a matter of design choice.

Those skilled in the art will appreciate that each of the grids 14,18 can be formed using a continuous wire that is folded back on itself to form the parallel adjacent wiring in the grid, or separate individual wire segments can be used, or a combination thereof.

The detector 10 is formed so that fluid particles that contact the wire mesh 13 will bridge at least one insulated wire and one uninsulated wire. The liquid causes a measurable change in the capacitance between the two interwoven grids 14,18 in effect by altering the dielectric characteristic of the wire mesh. With no liquid present on the mesh 13, the capacitance between the two grids will be a function of the dielectric constant of the wire insulation, the total area of the wire mesh 13, the wire gauge, and the closeness of the spacing between the wires (i.e., the spatial density of the wires). The presence of liquids such as water on the wire mesh 13 causes small changes in the admittance between wires that are bridged by the fluid particles, hence the overall capacitance between the two grids 14,18 is changed. For example, if the fluid being detected is a highly conductive fluid such as water, water particles adhering to the wire mesh 13 would tend to lower the measured capacitance of the detector 10 as compared to the capacitance of the detector 10 under dry conditions.

As illustrated in FIG. 1, the detector 10 includes a peripheral mesh flange portion 22 that extends transversely from the primary mesh region 13 and generally parallel to the longitudinal axis 12 of the conduit. This peripheral flange 22 lies flush up against an inner surface of wall 24 of the conduit and may be press fit to conform to the shape of the conduit. The mesh flange portion 22, therefore, contacts and detects liquid particles that travel along the inner surface 24 of the conduit.

This condition may occur, for example, when condensate forms on the conduit, or in a weightless environment. In the latter situation particularly, pressure from the gas flowing through the conduit forces entrained liquid particles out towards the conduit wall in all directions, and helps propel the liquid particles along the wall. Of course, in a gravity environment, entrained liquid particles may also collect on and flow along the bottom of the conduit due to the pull of gravity.

The conduit is preferably connected to electrical ground as by a wire 21 connected to a post 23. This aspect of the invention helps reduce the risk of electrical shock to personnel that may be near the conduit. Also, the grounded conduit acts as a shield for the detector 10 positioned therein against electromagnetic interference that could otherwise cause false capacitance measurements of the detector 10. Because one of the wire grids is made from uninsulated wire, the capacitance detector 10 is used preferably with one plate grounded. The peripheral mesh flange 22 directly contacts the grounded conduit inner surface 24, therefore, all the exposed uninsulated wire of grid 18 will be electrically at the same ground potential as the conduit. One of the uninsulated wires 20a may also be connected to the post 23 to improve the ground connection. Another wire 19 passes through the conduit and is insulated therefrom for connecting the detector 10 to the detector circuit 40.

Figure 2A:
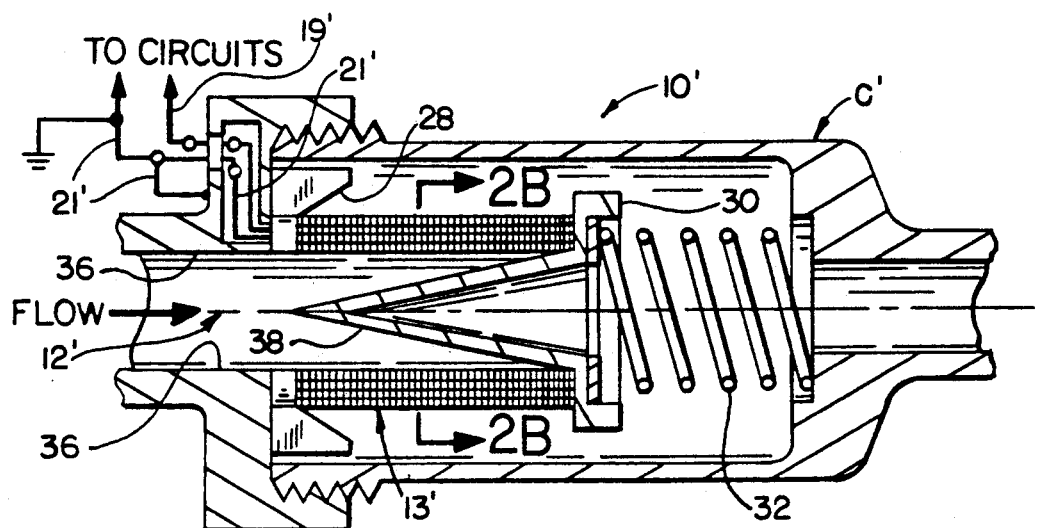
FIG. 2a is a schematic in partial longitudinal cross-section of an alternative embodiment of a liquid presence detector according to the present invention.
Figure 2B:
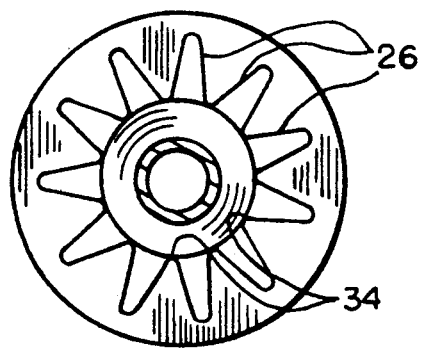
FIG. 2b is a transverse cross-sectional view of the liquid presence detector shown in FIG. 2 taken along the line 2b—2b.

With reference now to FIGS. 2a and 2b, an alternative embodiment of a liquid presence detector 10' according to the present invention is illustrated. In this embodiment, the detector 10' is a generally cylindrical element placed in the conduit C' coaxial with the conduit longitudinal axis 12'. The detector 10' is a wire mesh formed of two interwoven wire grids (one insulated, the other uninsulated) in a manner similar to the mesh 13 described with reference to FIG. 1. The mesh 13', however, is shaped into a somewhat cylindrical form, and as best shown in FIG. 2b, has a plurality of radial pleats 26. The mesh 13, can be conveniently seated in a retainer 28 and removably secured therein by a plate 30 held in place by a spring 32. The detector 10' is appropriately sized so that the inner radius 34 of the pleats 26 is generally flush with the inner surface 36 of the conduit to contact liquid particles traveling along the conduit wall. Also, the uninsulated wire grid of the mesh can contact the grounded conduit at the retainer 28 or be hardwired thereto as by a wire 21'. Again, wire 19' passes through the conduit and is insulated therefrom to electrically connect the detector 10 to the circuitry 40.

A gas flow distributor 38 may be provided and positioned within at least a portion of the detector 10'. The flow distributor 38 is a cone shaped element that causes the gas fluid to flow outwardly through the detector 10'. Liquid particles entrained in the gas fluid will therefore contact the capacitive detector 10'.

The wire mesh detector 10' shown in FIG. 2 functions electrically in the same way as the detector 10 in FIG. 1. The wire mesh is a two plate capacitor with each capacitor plate formed by a wire grid. One of the grids is made of insulated wire, and is interwoven in the described manner with a wire grid made of uninsulated wire. The grids may be formed from continuous wire or built up from individual wires or a combination thereof. When a liquid particle contacts the mesh, the particle bridges at least one pair of insulated and uninsulated wires to change the capacitance between the two interwoven wire grids, as explained hereinbefore. The conduit is electrically grounded so that one plate of the detector 10' capacitor is also at electrical ground during operation.

Figure 3:
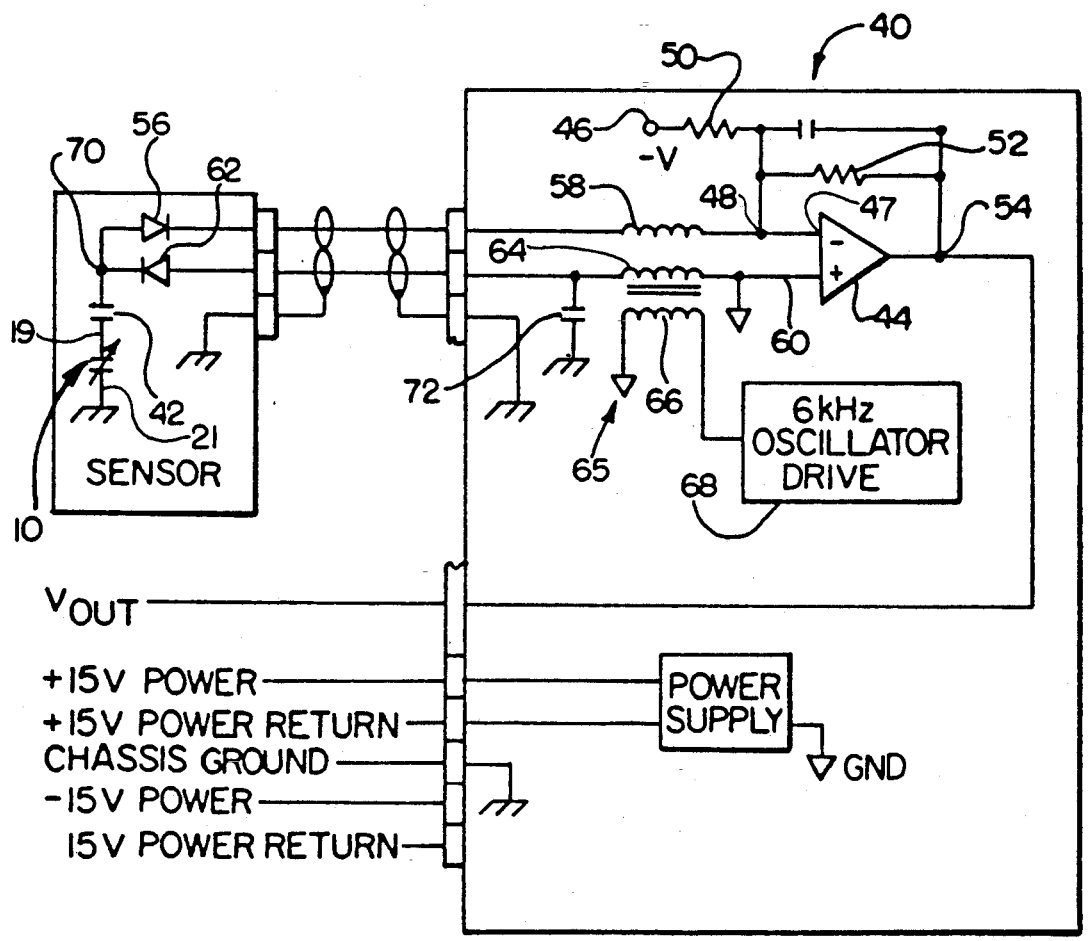
FIG. 3 is an electrical schematic of a circuit that can be used to measure capacitance of the liquid presence detectors illustrated in FIGS. 1 and 2.

With reference to FIG. 3, a preferred circuit for detecting the capacitance of the detectors 10 and 10' of FIGS. 1 and 2 is generally designated by the numeral 40. The circuit is described herein with respect to the detector 10, it being understood that this description is similarly applicable to the detector 10' embodiment. The detector 10 is represented as being electrically connected in series between electrical ground and a reference capacitor 42. The detector capacitor 10 shown schematically in FIG. 3, of course, has one plate formed by the uninsulated grid 18 that is in contact with the grounded conduit C, and the other plate formed by the insulated grid 14 which is connected to the circuit 40 by the wire 19. The use of a reference capacitor provides a convenient capacitance value for the circuit 40 to measure when no liquid is present on the detector 10, however, use of the reference capacitor is largely a matter of design choice.

The circuit 40 preferably includes an operational amplifier 44 (hereinafter "op-amp" 44) configured to function as an inverting summing amplifier. A DC bias voltage 46 is applied to the inverting input 47 of the op-amp 44 through an input resistor 50. A feedback resistor 52 is connected across the inverting input 47 and the op-amp output terminal 54. For convenience the input resistor 50 and the feedback resistor 52 may be of the same value so that the op-amp acts as a unity gain amplifier with respect to the bias voltage 46.

The detector 10 and reference capacitor 42 are connected to the inverting input of the op-amp 44 by a serially connected diode 56 and inductor 58. The detector 10 and reference capacitor 42 are connected to the non-inverting input 60 of the op-amp 44 by a serially connected second diode 62 and a secondary winding 64 of a transformer 65.

A primary winding 66 of the transformer 65 is connected to an AC oscillator 68 that produces, for example, a 6 kilohertz sine wave voltage across the primary winding 66.

The two diodes 56,62 are connected to provide a positive half-wave rectified signal at the common diode node 70. The diode 56 provides DC isolation of the signal at node 70 from the virtual ground at the summing node 48. The inductor 58 functions as a low frequency filter that passes DC rectified signals from the detector 10 to the summing node 48. A high frequency bypass capacitor 72 is provided to shunt high frequency noise to ground. Also, the non-inverting input 60 is connected to ground so that the op-amp functions as an inverting voltage gain summing amplifier.

The circuit 40 operates as follows. The oscillator 68 applies an AC signal to the circuit via the transformer 65. The detector 10 and reference capacitor 42 in combination with the diode 62 forms a half-wave rectifier for the AC signal applied from the oscillator 68. The half-wave rectified signal generated at node 70 is filtered through the inductor 58 and summed with the bias voltage 46 at the summing node 48. The summing node 48 is, of course, the same potential node as the inverting input to the op-amp 44. The output voltage at the op-amp output terminal 54 is the sum of the bias voltage 46 and the voltage produced by the half-wave rectification of the AC excitation signal. The DC voltage level produced by the half-wave rectifier will be a function of the capacitance of the detector 10 added to the value of the reference capacitor 42. The magnitude of the bias voltage 46 and the amplitude of the applied AC signal from the oscillator can be adjusted, as well as the value of the reference capacitor 42, so that under a known condition of no liquid on the detector 10, the output 54 from the op-amp 44 is a convenient number such as zero volts. When liquid particles adhere to the capacitor detector 10 as described hereinbefore, the capacitance between the interwoven grids 14,18 changes and is detected as a change in the output voltage of the op-amp 44. The op-amp output voltage changes in relation to the change in capacitance of the detector 10 because the capacitance of the detector affects the DC voltage level produced by rectification of the applied AC excitation signal 68.

The present invention also contemplates a new method for detecting liquid particles in a gas fluid conduit as explained in connection with the description of the preferred embodiments hereinbefore. Accordingly, this method includes the steps of forming a liquid presence detector as a capacitor sensor from a pair of interwoven wire grids with one grid being insulated wire and the other grid being uninsulated wire; placing the capacitor sensor in the conduit and using the wire grid to detect liquid particles that travel along the inner surface of the conduit as well as liquid particles that are entrained in the gas fluid; connecting the conduit to electrical ground and placing the wire grid sensor in the conduit in such a manner that uninsulated wires of the grid contact the conduit; and measuring changes in the capacitance of the wire grid due to contact of liquid particles with the grid. The new method also can be modified to include the step of forming the capacitor sensor into a generally cylindrical shape with a plurality of pleats therein and placing the sensor in the conduit coaxial with a longitudinal axis of the conduit so that liquid particles traveling along the conduit wall or inner surface contact the interwoven grid. An additional step in accordance with the present invention can be the use of a flow distributor positioned within at least a portion of the cylindrical detector to direct flow of the gas fluid and liquid particles towards the cylindrical capacitive detector.

Those skilled in the art will appreciate that modifications will be apparent and still within the spirit and scope of the claimed invention. For example, the circuit 40 illustrated in FIG. 3 is only one of many types of circuits that can conveniently be used to measure the capacitance between the wire and the conduit. While the invention has been shown and described with respect to specific embodiments thereof, this is for the purpose of illustration rather than limitation, and other variations and modifications of the specific embodiments herein shown and described will be apparent to those skilled in the art within the intended spirit and scope of the invention as set forth in the appended claims.

We claim:

1. A liquid presence detector for a gas conduit comprising a planar wire mesh having at least two interwoven wire grids, one of said wire grids being insulated, and the other of said wire grids being uninsulated; said wire mesh grids forming respective plates of a capacitor; said conduit being electrically grounded and said wire mesh being positioned in the conduit transverse a longitudinal axis of the conduit; said wire mesh having a peripheral portion thereof extending axially along and in contact with a portion of an inner surface of the conduit for contacting fluid particles traveling along said inner surface; and capacitance measuring means to measure changes in said wire mesh capacitance caused by fluid contacting said wire mesh.

2. The liquid presence detector according to claim 1 wherein said wire grids are interwoven in a criss-cross manner such that all insulated wires are generally parallel to each other and all uninsulated wires are generally parallel to each other and transverse said insulated wires.

3. The liquid presence detector according to claim 2 wherein each of said wire grids is formed by a single wire looped back on itself in a single plane to form a series of generally parallel wire sections interwoven with wire sections of the other wire grid.

4. The liquid presence detector according to claim 3 wherein said insulated wire grid is connected to said capacitance measuring means with said grounded conduit providing a reference potential for said capacitance measuring means.

5. A liquid presence detector connectable to a capacitance measuring circuit for use in a gas conduit comprising a wire mesh having at least two interwoven wire grids, one of said wire grids having an insulative coating thereon, and the other of said wire grids being uninsulated wire; said wire mesh grids forming respective plates of a capacitor; said conduit being electrically grounded and said wire mesh having a portion of said uninsulated grid in contact with the conduit; said wire mesh being in fluid communication with the conduit such that liquid particles traveling along an inner surface of the conduit contact said wire mesh; said insulated wire grid being electrically connectable to the capacitance measuring circuit.

6. The liquid presence detector for a gas conduit according to claim 5 wherein the conduit has a longitudinal axis and said wire mesh has an open cylindrical shape with said wire grids extending axially along a portion of the conduit.

7. The liquid presence detector for a gas conduit according to claim 6 further comprising a flow distributor within a portion of said wire mesh that directs gas flow in a nonaxial direction.

8. The liquid presence detector for a gas conduit according to claim 5 wherein said wire mesh is a generally planar screen positioned transverse a longitudinal axis of the conduit and having a portion thereof extending axially along and in contact with an inner surface of the conduit.

9. A method for detecting liquid particles in a gaseous fluid conduit comprising the steps of:
   a) providing in the conduit a capacitor mesh formed by two interwoven wire grids, one of said grids being insulated and the other said grid being uninsulated;
   b) connecting the conduit to electrical ground;
   c) positioning the capacitor in the conduit such that a portion of the capacitor mesh contacts an inner surface of the conduit; and
   d) using the capacitor mesh for detecting liquid particles in the conduit by measuring the capacitance between the two wire grids.

10. The method for detecting liquid particles in a gaseous fluid conduit according to claim 9 wherein the step of providing a capacitor mesh includes the step of forming the capacitor mesh as a generally planar screen with insulated wires being disposed parallel to each other and uninsulated wires being disposed generally parallel to each other and transverse the insulated wires.

11. The method for detecting liquid particles in a gaseous fluid conduit according to claim 9 wherein the capacitor mesh is formed in a generally open cylindrical shape positioned coaxially within the conduit.

12. The method for detecting liquid particles in a gaseous fluid conduit according to claim 11 further including the step of providing a flow distributor within a portion of said capacitor mesh cylinder.

13. A liquid presence detector connectable to a capacitance measuring circuit for use in a gas conduit comprising a planar wire mesh having at least two interwoven wire grids, one of said wire grids being insulated, and the other of said wire grids being uninsulated, said wire mesh grids forming respective plates of a capacitor; said wire mesh being positionable in fluid communication with the conduit such that particles traveling through said conduit contact said wire mesh thereby changing the capacitance thereof.

14. A liquid presence detector according to claim 13 wherein said wire mesh is positionable within the conduit with a portion of said wire mesh contacting an inner surface of the conduit such that liquid particles traveling along the conduit inner surface contact said wire mesh.

15. A liquid presence detector according to claim 14 wherein the conduit is electrically grounded.

16. A liquid presence detector according to claim 15 wherein said wire mesh is positionable transverse a longitudinal axis of the conduit.

17. A liquid presence detector according to claim 15 wherein said uninsulated wire grid contacts the grounded conduit.

18. A method for detecting liquid particles in a gaseous fluid conduit comprising the steps of:
 a) providing in the conduit a capacitor mesh formed by two interwoven wire grids, one of said grids being insulated and the other of said grids being uninsulated;
 b) positioning the capacitor mesh in fluid communication with the conduit; and
 c) using the capacitor mesh for detecting liquid particles in the conduit by measuring the capacitance between the two wire grids.

19. The method for detecting liquid particles according to claim 18 wherein the step of positioning the capacitor mesh in the conduit includes the step of electrically grounding the conduit.

20. The method for detecting liquid particles according to claim 19 wherein the capacitor mesh is positioned in the conduit such that liquid particles traveling along the conduit interior surface contact the wire mesh.

* * * * *